United States Patent [19]

Davis et al.

[11] Patent Number: 4,758,323
[45] Date of Patent: Jul. 19, 1988

[54] ASSAY SYSTEMS USING MORE THAN ONE ENZYME

[75] Inventors: Graham Davis, Bedforshire; Hugh A. O. Hill, Oxford, both of United Kingdom

[73] Assignee: Genetics International, Inc., Cambridge, Mass.

[21] Appl. No.: 607,698

[22] Filed: May 7, 1984

[30] Foreign Application Priority Data

| May 5, 1983 | [GB] | United Kingdom | 8312259 |
| May 5, 1983 | [GB] | United Kingdom | 8312265 |
| Jun. 9, 1983 | [GB] | United Kingdom | 8323801 |
| Jun. 9, 1983 | [GB] | United Kingdom | 8323800 |
| Feb. 29, 1984 | [GB] | United Kingdom | 8405262 |
| Feb. 29, 1984 | [GB] | United Kingdom | 8405263 |

[51] Int. Cl.$^4$ .......................................... G01N 27/46
[52] U.S. Cl. ................... 204/403; 204/1 T; 435/26; 435/288; 435/817
[58] Field of Search .................. 435/26, 288, 817; 204/403, 1 E

[56] References Cited

U.S. PATENT DOCUMENTS

| 4,224,125 | 9/1980 | Nakamura et al. | 204/1 E |
| 4,225,410 | 9/1980 | Pace | 204/1 E |
| 4,271,265 | 6/1981 | Deneke et al. | 435/26 |
| 4,318,980 | 11/1983 | Boguslaski et al. | 435/7 |
| 4,376,689 | 3/1983 | Nakamura et al. | 435/817 |
| 4,416,983 | 11/1983 | Roder et al. | 435/25 |
| 4,427,771 | 1/1984 | Misaki et al. | 435/26 |
| 4,446,231 | 5/1984 | Self | 435/26 |
| 4,463,090 | 7/1984 | Harris | 435/7 |
| 4,490,464 | 12/1984 | Gorton et al. | 435/817 |
| 4,545,382 | 10/1985 | Higgins et al. | 204/403 |

FOREIGN PATENT DOCUMENTS

| 0078636 | 11/1983 | European Pat. Off. | |
| WO82/03729 | 10/1982 | PCT Int'l Appl. | 435/817 |

*Primary Examiner*—T. Tung

[57] ABSTRACT

This specification discloses methods of detection or measurement of an enzyme or of its specific substrate, and sensors used in such methods. The present invention is concerned with a multi-enzyme system, and the specification discloses, as one aspect of the invention a method of assay in which an electrode poised at a suitable potential is contacted with a system comprising a first enzyme, a cofactor linked with said enzyme and a mediator compound which transfers charge to the electrode from the first enzyme when its electrical state is changed by reaction of cofactor material.

The cofactor may be NAD, NADP (both collectively referred to herein as NAD(P)), cAMP, ATP, GTP, TTP, or CTP.

The specification particularly illustrates a method of assay in which an electrode (1) poised at a suitable potential is contacted with a system comprising a first enzyme $E_1$ a nicotinamide adenine dinucleotide compound N linked with said enzyme $E_1$ and a mediator compound F which transfers charge to the electrodes from the first enzyme when its electrical state is changed by a NAD(P) NAD(P)H reaction. The NAD compound may act as a "bridge" between the said enzyme/mediator system and further NAD utilizing enzyme E2.

7 Claims, 1 Drawing Sheet

ASSAY SYSTEMS USING MORE THAN ONE ENZYME

This invention relates to methods of detection or measurement of an enzyme or of its specific substrate, and to sensors used in such methods.

The following commonly owned, co-pending United States patent application filed May 7, 1984 are hereby incorporated by reference:

| Title | Inventors | Ser. No. |
|---|---|---|
| 1. Analytical Equipment and Sensor Electrodes Therefor | Higgin et al. | 607,599 |
| 2. Assay Techniques Using Specific Building Systems | Hill | 607,695 |
| 3. Assay Techniques Utilizing More Than One Enzyme | Davis et al. | 607,607 |

Our European Patent Application No. 82305597 describes and claims a sensor electrode which comprises at least at an external surface thereof a combination of an enzyme and a mediator compound which transfers charge to the electrode when the enzyme is catatytically active. Such an electrode, when contacting the specific substrate for the enzyme and poised at a suitable potential gives a signal responsive to the presence of, or indicative of the extent of the enzyme/substrate reaction, even in a complex mixture of substrates since the enzyme is specific to the desired substrate component.

The practical operation of such a system depends upon the incorporation of the mediator compound. A number of types of such compounds are disclosed in that Application, such as polyviologens, fluoranil, chloroanil, etc; but the mediators with best characteristics are metallocenes.

Ferrocenes (bis-cyclopentadienyl iron and its derivatives) fall within the last above named group and have advantages over other mediators used with enzyme/substrate reactions for charge-transfer purposes. The unique structure and properties of ferrocene and its derivatives have resulted in a considerable amount of theoretical and experimental study. First synthesised in 1951, ferrocene was the earliest example of the now well-known metallocene compounds. Whilst ferrocenes had been found to be of limited value in spectrophotometric assays as a result of their poor solubility in aqueous solution and low extinction coefficients, they have been found to be more suited to a bio-electrochemical system. Ferrocenes have:

(a) a wide range of redox potentials accessible through substitution of the cyclopentadienyl rings which can be functionalised;
(b) electrochemically reversible one-electron redox properties;
(c) the pH-independent redox potential and the slow autoxidation of the reduced form.

These compounds lend themselves to the formation of derivatives, e.g. by substitution of one or both cylopentadienyl rings and/or by polymerisation. We have studied a number of derivatives of ferrocene such as those listed in the table below;

| Ferrocene derivative | $E^o$ | Solubility | E |
|---|---|---|---|
| 1,1'-dimethyl- | 100 | I,D | — |
| acetic acid | 124 | S | 370 |
| hydroxyethyl- | 161 | S | — |
| ferrocene | 165 | I,D | 335 |
| 1,1'bis(hydroxymethyl)- | 224 | S | 385 |
| monocarboxylic acid | 275 | S | 420 |
| 1,1'-dicarboxylic acid | 385 | S | — |
| chloro- | 345 | I,D | — |
| methyl trimethylamino- | 400 | S | — |

S indicates water solubility; I,D means respectively insoluble and detergent-solubilised in 3% Tween-20.
$E^o$ is in mV vs a standard calomel electrode, E is measured in $cm^{-1} M^{-1}$.

The $E^o$ values of various ferrocenes in phosphate buffer at pH 7.0 given in the above table, span a range of potentials, $E^o = 100$ to 400 mV vs SCE. The trend in $E^o$ values is in agreement with that expected on the basis of substituent effects. In general electron-donating groups stabilize the positive charge and hence promote oxidation more so than electron withdrawing groups.

Of these we find 1,1-dimethylferrocene and ferrocene monocarboxylic acid to be generally preferable because of their particularly wide range of accessible enzymes.

Although the invention described in our earlier Application was particularly adapted to the use of glucose as the substrate and of glucose oxidase or dehydrogenase as the enzyme (thereby to provide, for example, a glucose sensor of use in the diagnosis of diabetic conditions), other enzyme/substrate pairs whose electrochemical behaviour in association with mediator compounds which have been studied by the Applicants include the following:

| Enzyme | Substrate |
|---|---|
| Flavo-proteins | |
| Pyruvate Oxidase | Pyruvate |
| L-Amino Acid Oxidase | L-Amino Acids |
| Aldehyde Oxidase | Aldehydes |
| Xanthine Oxidase | Xanthines |
| Glucose Oxidase | Glucose |
| Glycollate Oxidase | Glycollate |
| Sarcosine Oxidase | Sarcosine |
| Lactate Oxidase | Lactate |
| Glutathione Reductase | NAD(P)H |
| Lipoamide Dehydrogenase | NADH |
| PQQ Enzymes | |
| Glucose Dehydrogenase | Glucose |
| Methanol Dehydrogenase | Methanol and other Alkanols |
| Methylamine Dehydrogenase | Methylamine |
| HAEM-Containing Enzymes | |
| Lactate Dehydrogenase | Lactate |
| Horseradish Peroxidase | Hydrogen Peroxidase |
| Yeast Cytochrome C Peroxidase | Hydrogen Peroxidase |
| Metalloflavoproteins | |
| Carbon monoxide Oxidoreductase | Carbon Monoxide |
| Cuproproteins | |
| Galactose Oxidase | Galactose |

Of these, it was found clearly advantageous to utilize those enzyme/substrate pairs whose behaviour was established in most detail and which give good, preferably linear, response over the expected measurement range.

That earlier Application was predominantly concerned with sensors where mediator and enzyme were both present on the electrode for contact with the substrate. Useful sensors, their nature and their manufacture, and equipment for facilitating their use, are all disclosed in more detail in our co-pending Application Ser. No. 607,599 entitled "Analytical Equipment and Sensor Electrodes Therefor" filed of even date herewith the disclosure of which is incorporated herewith by way of reference.

However, the system is the same if all the mediator, enzyme, and substrate are in solution, or if the sensor only carries mediator and enzyme, or even only mediator alone.

Our co-pending Application of even date Ser. No. 607695 entitled "Assay Techniques Utilising Specific Binding Agents" utilises the basic system on a solution basis and assays specific binding reactions (e.g. antigen-/antibody reactions or reactions of nucleic acid probe/-target sequence) by their effect on the electrochemical availability of enzyme or mediator or both. Its disclosure, especially of liquid-based systems, is incorporated herein by way of reference.

All of the above Applications are primarily concerned with single enzyme systems. Our further co-pending Application entitled "Assay system utilising more than one enzyme" describes and claims an invention in which a further enzyme (in the liquid or on the electrode) acts on its specific substrate to affect the level of the mediator-linked-enzyme substrate. This can be done by complete conversion, in one or more stages e.g. from a substrate such as creatinine via creatine to sarcosine, which can be acted on by its mediator/linked oxidase to give a reading from which the creatinine level can be derived. It can also be done by more or less complex schemes of competitive reaction for the same substrate e.g. by mediator-linked glucose oxidase competing with an ATP-driven kinase yielding a glucose phosphate; the extent of competitive reaction being a measure of ATP or kinase, whichever is unknown.

The disclosure of the above Application, discussing multi-enzymes linked by substrate changes, is also incorporated herein by way of reference.

The present invention is also concerned with a multi-enzyme system, but has a different type of internal system linkages from the substrate-linked chain of reactions disclosed in our co-pending Application.

In one aspect the invention provides a method of assay in which an electrode poised at a suitable potential is contacted with a system comprising a first enzyme, a cofactor linked with said enzyme and a mediator compound which transfers charge to the electrode from the first enzyme when its electrical state is changed by reaction of cofactor material.

The cofactor may be NAD, NADP (both collectively referred to herein as NAD(P)), cAMP, ATP, GTP, TTP, or CTP.

In a further aspect the invention consists of a method of assay in which an electrode poised at a suitable potential is contacted with a system comprising a first enzyme, a nicotinamide adenine dinucleotide compound linked with said enzyme and a mediator compound which transfers charge to the electrode from the first enzyme when its electrical state is changed by a NAD(P)/NAD(P)H reaction.

In the practical operation of the invention it is preferred to operate so that a second enzyme is also linked with the NAD(P) compound and a substrate for said second enzyme is present in the said system so that the substrate/second reaction causes the NAD(P) compound to undergo its reversible reaction and thus affect the first enzyme and transfer charge to the electrode in an amount correlated with the extent of second enzyme/substrate reaction so as to permit assay of either if the other is known.

As with our copending applications referred to herein, there are various modes of operation, with the active components variously distributed in the solution or on the electrode. Thus, a metal electrode may be dipped into a solution containing the mediator, both enzymes, the NAD(P) compound and the substrate. Alternatively, an electrode may be coated with mediator, both enzymes and the NAD(P) compound and is dipped into solution containing the substrate to detect substrate or measure its concentration. Alternatively again, an electrode may be coated with mediator, the first enzyme, the NAD(P) compound, and the substrate is dipped into a solution containing the second enzyme to detect the enzyme or measure its concentration.

Examples of specific enzymes, cofactors, mediators and substrates are given below. Moreover, the electrode, if made of noble metal such as gold, may be linked with thiol (or like sulphur) substituted ferrocenes, or the mediator may be chemically linked with its enzyme; both of these expedients are described in detail, with examples in our copending application entitled "Assays Systems Utilising Specific Binding Agents" referred to above and incorporated herein by way of reference.

The invention will be further described with reference to the accompanying drawings in which.

Figure 1:
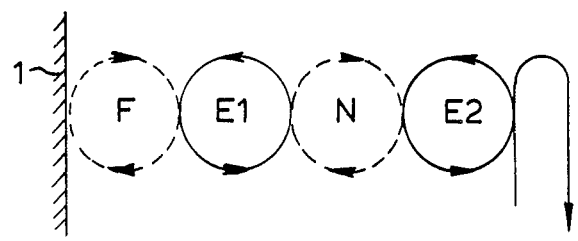
FIG. 1 shows a general scheme of linked enzymes used in the method of the invention.

The scheme shown in FIG. 1 shows an electrode 1 and four molecular species, namely: a mediator such as a ferrocene (F) preferably 1,1'dimethylferrocene in an immobilized system or ferrocene monocarboxylic acid in a freely diffusing system; an enzyme E1 capable of linking with the ferrocene electrochemically whereby the ferrocene transfers charge from the enzyme to the electrode; a nicotinamide adenine dinucleotide material N, as discussed in more detail below, and a second enzyme E2 specific to the substrate S which it converts to the reacted substrate RS.

A difference between the invention as shown in FIG. 1 and the invention described in our earlier applications resides in the linkage between E1 and N. Hitherto, our inventions have involved the transfer of charge from E1 to the electrode 1 whenever the enzyme E1 has been catalytically active upon its specific substrate. With the present invention there is no substrate for E1, but it is linked, as part of a chain of transfer of charge, to enzyme E2 by compound N whereby, when E2 acts on its substrate S, charge is eventually transferred down the chain to electrode 1.

The system can be embodied in many different ways. For example, a simple gold electrode 1 can be dipped into a mixed solution of F, E1, N, E2 and S to give, when poised against a reference electrode, a current dependent upon the extent of the enzyme catalysed S-RS reaction.

At the other extreme, F, E1, N and E2 can all be present at the surface of a composite electrode, to provide a sensor electrode to detect, or measure the level of, substrate S in a solution. If desired, the composite electrode could comprise F, E1, N, S, thereby giving a sensor whereby E2 can be assayed. Moreover, an electrode could comprise F, E1 and N only, to give an assay for the existence of an E2-catalysed S-SR reaction. Other combinations of immobilised and dissolved components, can also be envisaged by the man skilled in the art.

Figure 1A:
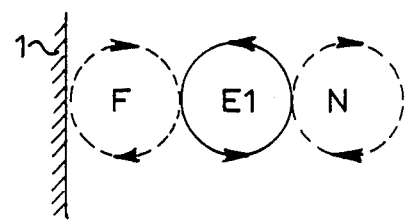
FIG. 1a shows an assay system as part of the above method.

The system can also be simplified as an assay for compound N, by omitting E2 and S, as shown in FIG. 1a.

Figure 2:
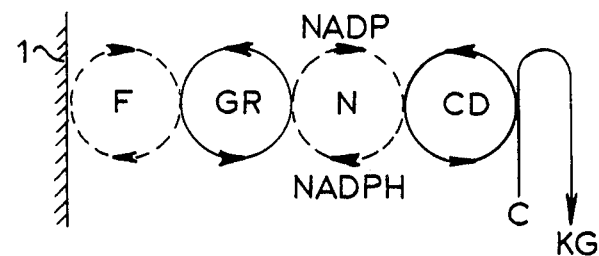
FIG. 2 shows a particular embodiment of the scheme utilising glutathione reductase as the linking enzyme.

FIG. 2 shows a particular example of the invention. In this example, F is, as described above, 1,1' dimethylferrocene. The enzyme E1 of FIG. 1 is embodied as glutathione oxidoreductase GR (E.C. 1.6.4.2). The compound N is nicotinamide adenine dinucleotide phosphate (NADP). The enzyme E2 is D-iso-citrate dehydrogenase (CD) EC 1.1.1.42, and its substrate S is accordingly D-iso citrate (C) which is converted by the enzyme to β-ketoglutarate (KG).

The system can be embodied using a gold electrode poised against SCE and in a solution containing ferrocene monocarboxylic acid, glutathione reductase, D-isocitrate dehydrogenase and NADP. Such a solution does not generate an electrode current, the gold giving no detectable side reactions.

When D-isocitrate was added, however, dehydrogenation took place to give α-keto glutarate, and yield the reduced form of the NADP i.e. NADPH. This in turn was reoxidised by the glutathione reductase, giving the reduced form of the GR enzyme, and this in turn reduced the ferricinium mediator ion which transfers charge to the electrode indicative of the D-isocitrate concentration.

Conversely, the system was also made up containing F+GR+NADP+substrate C, and provided an assay system for the enzyme D-isocitrate dehydrogenase. An assay system could also be constructed with cholesterol in solution thereby providing an assay for the enzyme 7-dehydrocholesterol reductase.

A similar choice of enzyme or substrate assay is possible with any of the following list of enzyme/substrate pairs.

| Enzyme | Substrate |
| --- | --- |
| D-isocitrate dehydrogenase | D-Isocitrate |
| Glutamate dehydrogenase | Glutamate |
| Glucose-6-phosphate dehydrogenase | Glucose-6-phosphate |
| 20-β-hydroxysteroid dehydrogenase | 20-α-hydroxysteroids |
| Glycerol dehydrogenase | Glycerol |
| Glycerol dehydrogenase (when coupled via lipase) | Triglycerides |
| Aldehyde dehydrogenase | Aldehydes |

The particular enzymes selected may be employed in solution or may be chemically bound to the surface of the electrode. The glutathione reductase may also be chemically bound to the surface of the electrode in certain embodiments.

The assay may be extended to a wide range of NADP-linked enzymes or other co-factor linked systems and this allows the construction of sensors over such a wide range of enzyme-catalysed reactions thereby allowing a corresponding wide range of equipment and end uses to be envisaged.

Thus, since many of the listed enzymes involve substrates other than naturally-occuring substrates, the use of the ferrocene-type mediators particularly assists the production of sensors for process control generally, including fermentation control, for incorporating in side-stream continous monitoring and control systems.

Figure 3:
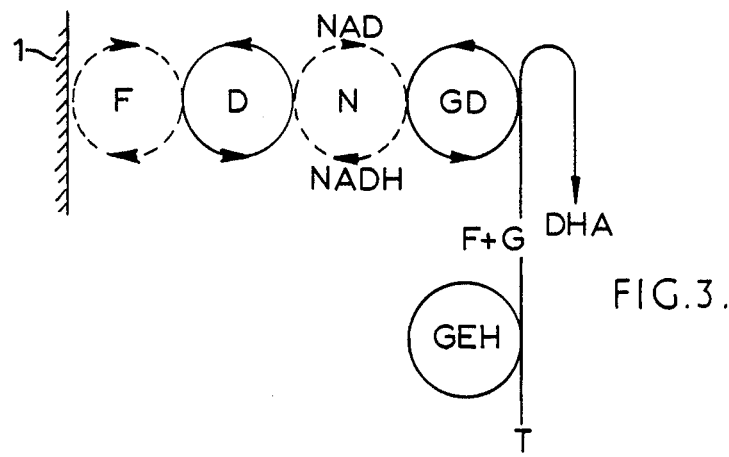
FIG. 3 shows another particular embodiment of the scheme utilising diaphorase as the linking enzyme.

FIG. 3 shows another particular example of the invention.

F is as before, ferrocene monocarboxylic acid. E1 is the enzyme diaphorase (D), otherwise known as dihydrolipoamide dehydrogenase E.C. 1.6, 4.3.), is isolated from *Clostridium Klugvini*, and is available from Boehringer. N is the nocotinamide adenine dinucleotide, NAD and E2 is a glycerol dehydrogenase GD. The system of FIG. 2 further comprises the provision of the necessary glycerol substrate of an enzyme catalysed reaction whereby triglycerides T are reacted with a lipase (glycerol ester hydrolase GEH) to a glycerol/fatty acid mixture.

A mixed solution was made up containing a soluble ferrocene monocarboxylic acid, diaphorase, NAD, glycerol dehydrogenase and glycerol ester hydrolase. No current was observed when the solution was contacted with a gold electrode poised at 150 mV vs. SCE. Addition of triglyceride led to the conversion by means of the GEH enzyme to glycerol and fatty acids and the glycerol component of this mixture was thereafter oxidised by enzyme GD to dihydroxyacetone (DHA). An electrical charge arising in dependence on the progress of this latter reaction was transferred down the chain of components and thus gave a measurable current, related to the original triglyceride level at the electrode.

It will be observed that the reaction of triglyceride to glycerol/fatty acid, and further reaction to dihydroxyacetone (DHA) is of itself an example of the invention in our copending Application also entitled "Assay system using more than one enzyme". In this earlier invention the two enzymes are "substrate-linked" i.e. the product of one reaction is the substrate of the next. In the present invention, the two enzymes are linked e.g. by NAD or NADP giving a cyclic reaction whereby the E1 and E2 are electrically linked.

EXAMPLE 3

1,1'-dimethylferrocene was deposited from toluene solution on to a carbon foil (GRAPHOIL) and diaphorase enzyme immobilised over the ferrocene using the carbodiimide material DCC (1-cyclohexyl-3(2-morpholino ethyl) carbodiimide metho-p-toluene sulphonate). This composite electrode was poised at +150° mv against SCE and immersed in a NAD/glycerol dehydrogenase solution which was quantitatively sensitive, as a current readout at the electrode, to glycerol additions.

Other NAD-linked enzymes used in this invention include the following list of enzymes given with their corresponding substrates:

| Enzymes | Substrate |
| --- | --- |
| Formate dehydrogenase | Formate |
| β-Hydroxybutyrate dehydrogenase | Blood ketones |
| Lactate dehydrogenase (either NAD-linked or cytochrome linked) | Lactate |
| Alcohol dehydrogenase | Alcohols |
| Malate dehydrogenase | Malates |
| Glycerate-1,3,-phosphate dehydrogenase | Glycerate-1, 3-phosphate |
| Galactose dehydrogenase | Galactose |
| Sorbitol dehydrogenase | Sorbitol |
| Glucose dehydrogenase (NADPH-dependent) | Glucose |

| Enzymes | Substrate |
| --- | --- |
| Cholesterol reductase | Cholesterol |
| NAD-linked Cholesterol dehydrogenase | Cholesterol |
| Steroid Dehydrogenases | NAD- or NADPH-dependent steroids |

The invention in this instance always comprises a mediator compound and an enzyme in the system. It does particularly lend itself to the provision of a chemically modified enzyme, that is to say, an enzyme in which the mediator group is chemically linked to the enzyme structure in such a way as not to destroy its enzymatic activity. We have found by way of example, that it is possible to introduce up to eight or even twelve ferrocene groups into a glucose oxidase enzyme, and that by analogy such chemical modification of enzymes can readily take place in the other possible enzymes and in this invention.

Several patent applications are described herein as "our" applications because they, together with this application, are commonly owned by Genetics International, Inc. All of the material disclosed in each of those applications is hereby incorporated by reference in this application.

We claim:

1. A sensor electrode having a coating consisting essentially of a ferrocene mediator, gluathione reductase and a nicotinamide adenine dinucleotide.

2. A sensor electrode as claimed in claim 1 in which the ferrocene is 1,1'-dimethylferrocene.

3. A sensor electrode as claimed in claim 1 in which the ferrocene and enzyme are chemically linked together.

4. The sensor electrode of claim 1 wherein said electrode is substantially free from substrate for said enzyme.

5. A sensor electrode having a coating consisting essentially of a ferrocene mediator, diaphorase, and a nicotinamide adenine dinucleotide.

6. A sensor electrode as claimed in claim 5 in which the ferrocene is 1,1'-dimethylferrocene.

7. A sensor electrode as claimed in claim 5 in which the ferrocene and enzyme are chemically linked together.

* * * * *